(12) United States Patent
Treves et al.

(10) Patent No.: US 6,548,821 B1
(45) Date of Patent: Apr. 15, 2003

(54) METHOD AND APPARATUS FOR INSPECTING SUBSTRATES

(75) Inventors: David Treves, Palo Alto, CA (US); Thomas A. O'Dell, Campbell, CA (US)

(73) Assignee: Komag, Inc., San Jose, CA (US)

( * ) Notice: Subject to any disclaimer, the term of this patent is extended or adjusted under 35 U.S.C. 154(b) by 0 days.

(21) Appl. No.: 09/549,501

(22) Filed: Apr. 14, 2000

Related U.S. Application Data

(63) Continuation-in-part of application No. 09/337,709, filed on Jun. 21, 1999.

(51) Int. Cl.$^7$ .............................................. G01N 21/88
(52) U.S. Cl. ........................... 250/559.45; 250/559.46; 250/559.48; 250/559.49
(58) Field of Search ....................... 250/559.45, 559.46, 250/559.48, 559.49

(56) References Cited

U.S. PATENT DOCUMENTS

| | | | |
|---|---|---|---|
| 3,679,307 A | | 7/1972 | Zoot et al. ...................... 356/4 |
| 3,999,865 A | * | 12/1976 | Milam et al. .......... 250/559.46 |

(List continued on next page.)

FOREIGN PATENT DOCUMENTS

| | | |
|---|---|---|
| EP | 0 793 092 | 9/1997 |
| JP | 50-80123 | 6/1975 |
| JP | 3-214423 | 9/1991 |
| JP | 8-14868 | 1/1996 |
| JP | 8014868 | 1/1996 |
| JP | 8-128965 | 5/1996 |
| JP | 9-26396 | 1/1997 |
| JP | 9-33446 | 2/1997 |
| JP | 10-134443 | 5/1998 |
| JP | 10-143801 | 5/1998 |
| JP | 10-260012 | 9/1998 |
| WO | WO 97/27467 | 7/1997 |
| WO | WO 98/44330 | 10/1998 |

OTHER PUBLICATIONS

Vlasta Cejna et al., "Design and Application of Optical Defect Detection System in the Production Process", Phase Metrics located in San Diego, California (total of four pages, pages unnumbered). possession before Jun. 21, 1999.
Silicon Photodiodes 1994 Catalog published by Centronic of Newbury Park, California, pp. 1,2, 13–15 and 31–38.

(List continued on next page.)

*Primary Examiner*—Robert H. Kim
*Assistant Examiner*—Pamela R. Hobden

(57) ABSTRACT

Substrate inspection apparatus in accordance with the invention comprises optics for reflecting a laser beam off of a substrate and a detector for detecting the reflected laser beam. If a defect is present at the point where the laser reflects off the substrate, the laser will be deflected at an angle. Circuitry coupled to the detector generates a first signal that provides a measure of the extent to which the laser beam is deflected. (This signal is a measure of the slope of the defect walls.) An integrator receives that signal, and generates a second signal that is the integral of the first signal. The second signal is a measure of the height of the defect. The first and second signals provide a measure of the types of defects present on the substrate, and are used to determine whether the substrate is acceptable or should be rejected. In accordance with a second embodiment of the invention, laser beams are reflected off both the top and bottom surfaces of the substrate and detected by detectors. Circuitry coupled to each detector generates a signal indicative of the extent to which each laser beam is deflected by defects. In this second embodiment, the integrator integrates the sum of these signals to generate an integral output signal. This integral output signal is insensitive to substrate vibration that can occur during testing.

21 Claims, 10 Drawing Sheets

U.S. PATENT DOCUMENTS

| | | | |
|---|---|---|---|
| 4,065,786 A | 12/1977 | Stewart | 358/128 |
| 4,092,068 A | 5/1978 | Lucas et al. | 356/73 |
| 4,355,904 A | 10/1982 | Balasubramanian | 356/376 |
| 4,395,122 A | 7/1983 | Southgate et al. | 356/237 |
| 4,402,607 A | 9/1983 | McVay et al. | 356/339 |
| 4,412,743 A | 11/1983 | Eberly | 356/237 |
| 4,544,241 A | 10/1985 | LaBudde | 350/486 |
| 4,600,996 A | 7/1986 | Kawauchi | 364/491 |
| 4,627,724 A | 12/1986 | Cameron | 356/141 |
| 4,629,319 A | 12/1986 | Clarke et al. | 356/237 |
| 4,766,512 A | 8/1988 | Bogdanski | 360/137 |
| 4,794,264 A | 12/1988 | Quackenbos et al. | 250/563 |
| 4,794,265 A | 12/1988 | Quackenbos et al. | 250/572 |
| 4,920,385 A | 4/1990 | Clarke et al. | 356/237 |
| 4,933,552 A | 6/1990 | Lee | 250/310 |
| 4,943,734 A | 7/1990 | Johnson et al. | 250/572 |
| 5,153,844 A | 10/1992 | Beni et al. | 364/560 |
| 5,155,371 A | 10/1992 | Burggraf et al. | 250/563 |
| 5,189,481 A | 2/1993 | Jann et al. | 356/73 |
| 5,212,677 A | 5/1993 | Shimote et al. | 369/58 |
| 5,377,001 A | 12/1994 | Malin et al. | 356/237 |
| 5,377,002 A | 12/1994 | Malin et al. | 356/237 |
| 5,389,794 A * | 2/1995 | Allen et al. | 250/559.48 |
| 5,428,452 A | 6/1995 | Grycewicz | 356/430 |
| 5,602,639 A | 2/1997 | Kohno | 356/237 |
| 5,644,400 A | 7/1997 | Mundt | 356/400 |
| 5,661,559 A | 8/1997 | Brezoczky et al. | 356/353 |
| 5,719,840 A | 2/1998 | Jann | 369/58 |
| 5,781,649 A | 7/1998 | Brezoczky | 382/108 |
| 5,818,592 A | 10/1998 | Womack et al. | 356/357 |

OTHER PUBLICATIONS

Optoelectronic Components Catalog, published by UDT Sensors, Inc, of Hawthorne, California, pp.1 and 28–37. published before Jun. 21, 1999.

Optoelectronics DataBook published by Advanced Photonics, Inc. of Cammarillo, California, pp. 32–35. published before Jun. 21, 1999.

Dialog Printout regarding Japanese references 5–56459, which reference was published in 1993.

* cited by examiner

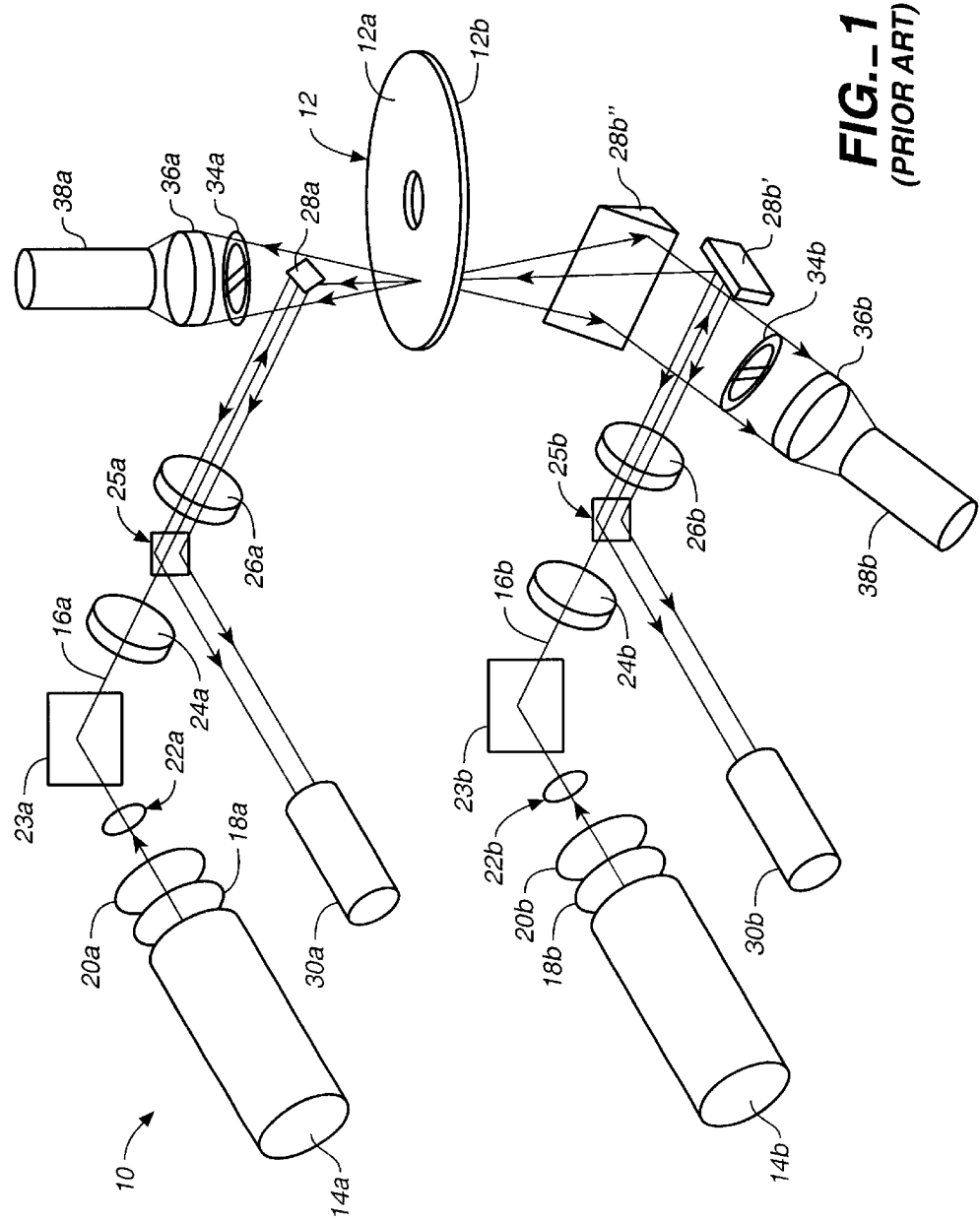
FIG._1 (PRIOR ART)

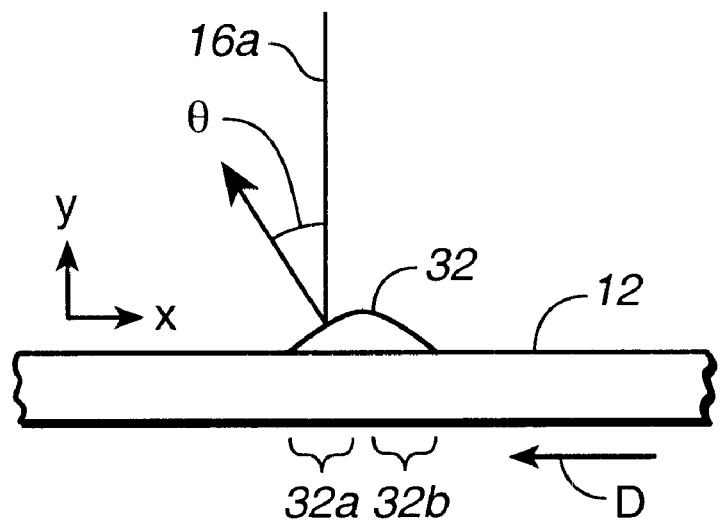
FIG._2A
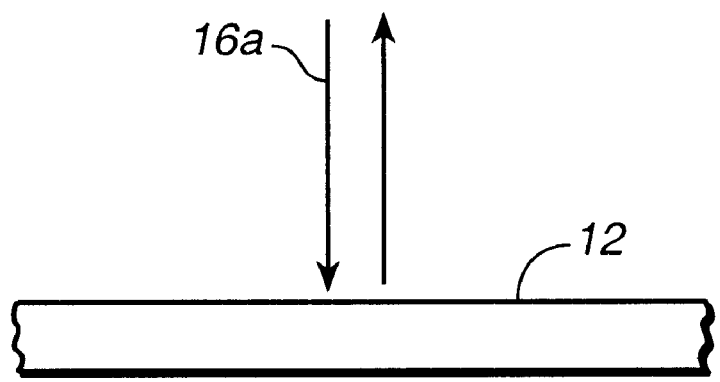
FIG._2B

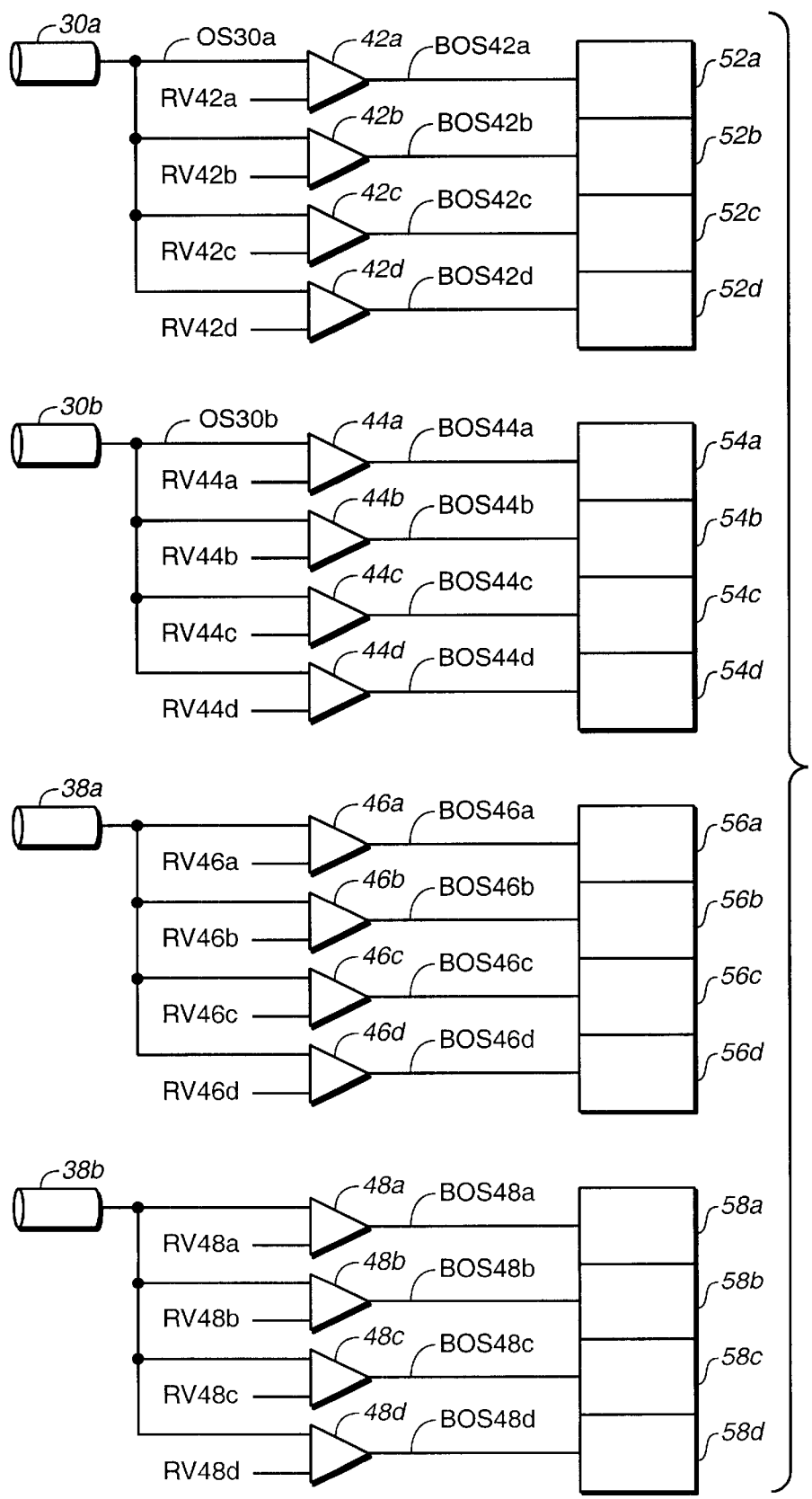
FIG._3
*(PRIOR ART)*

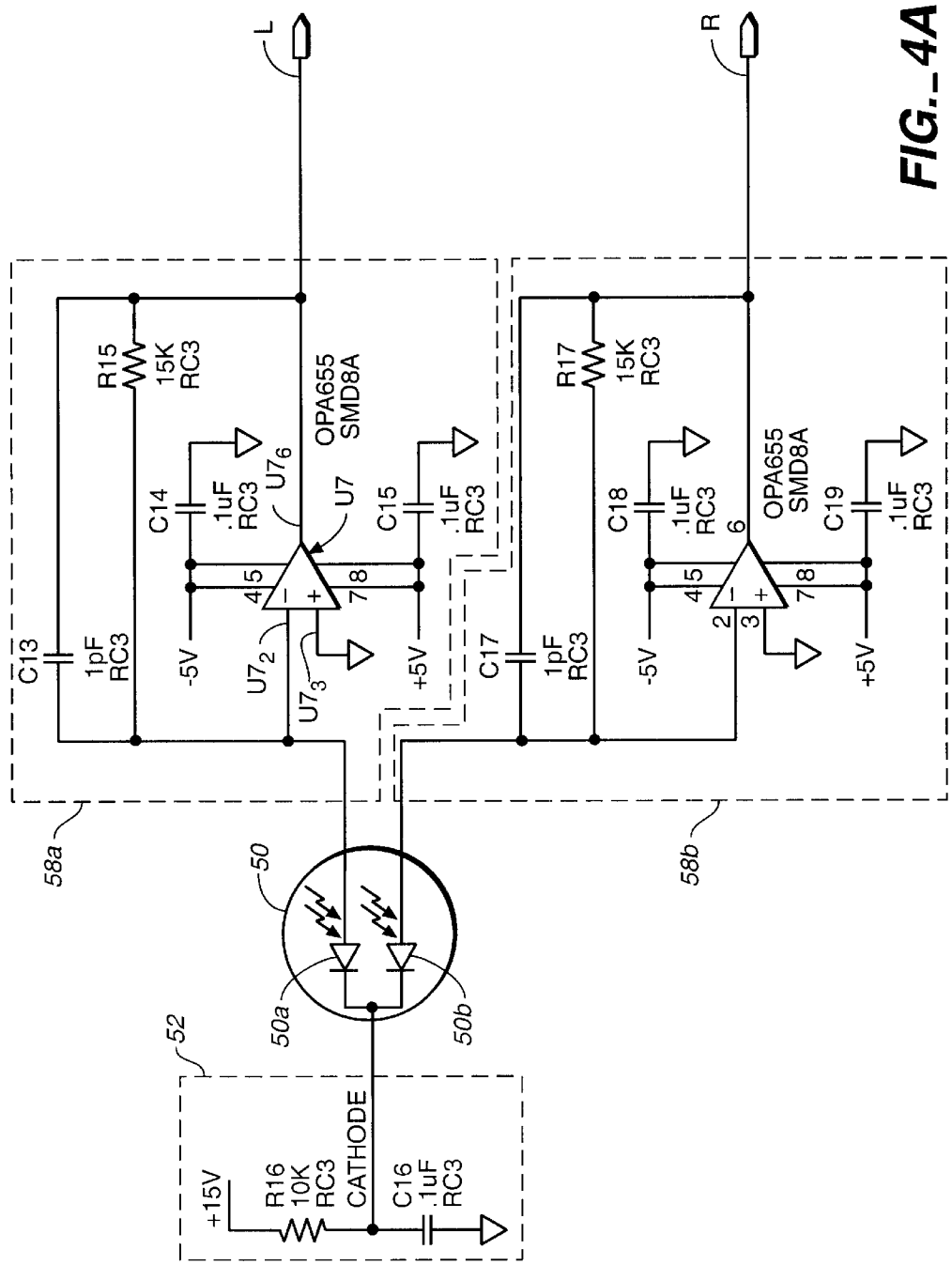
FIG._4A

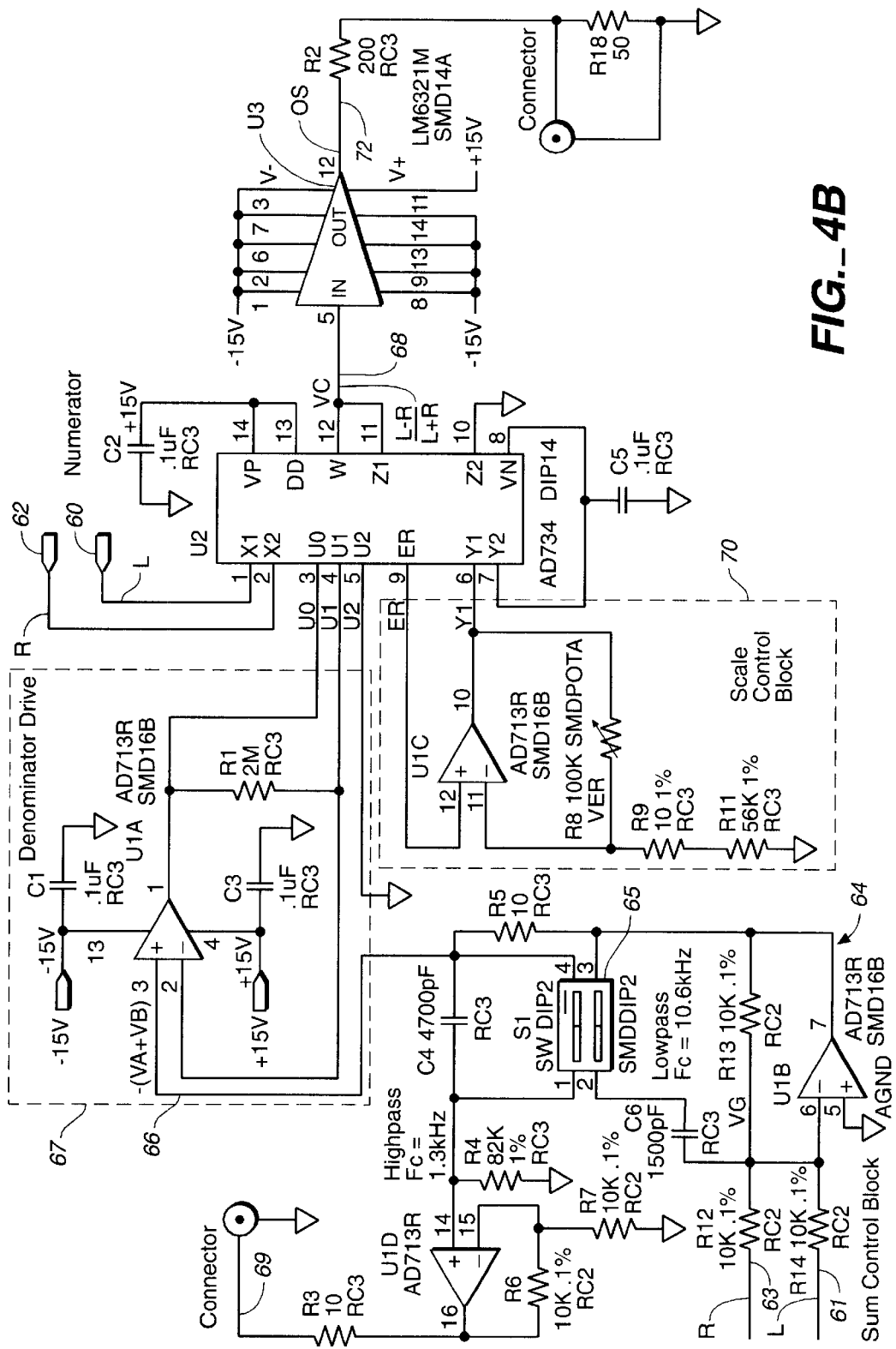
FIG._4B

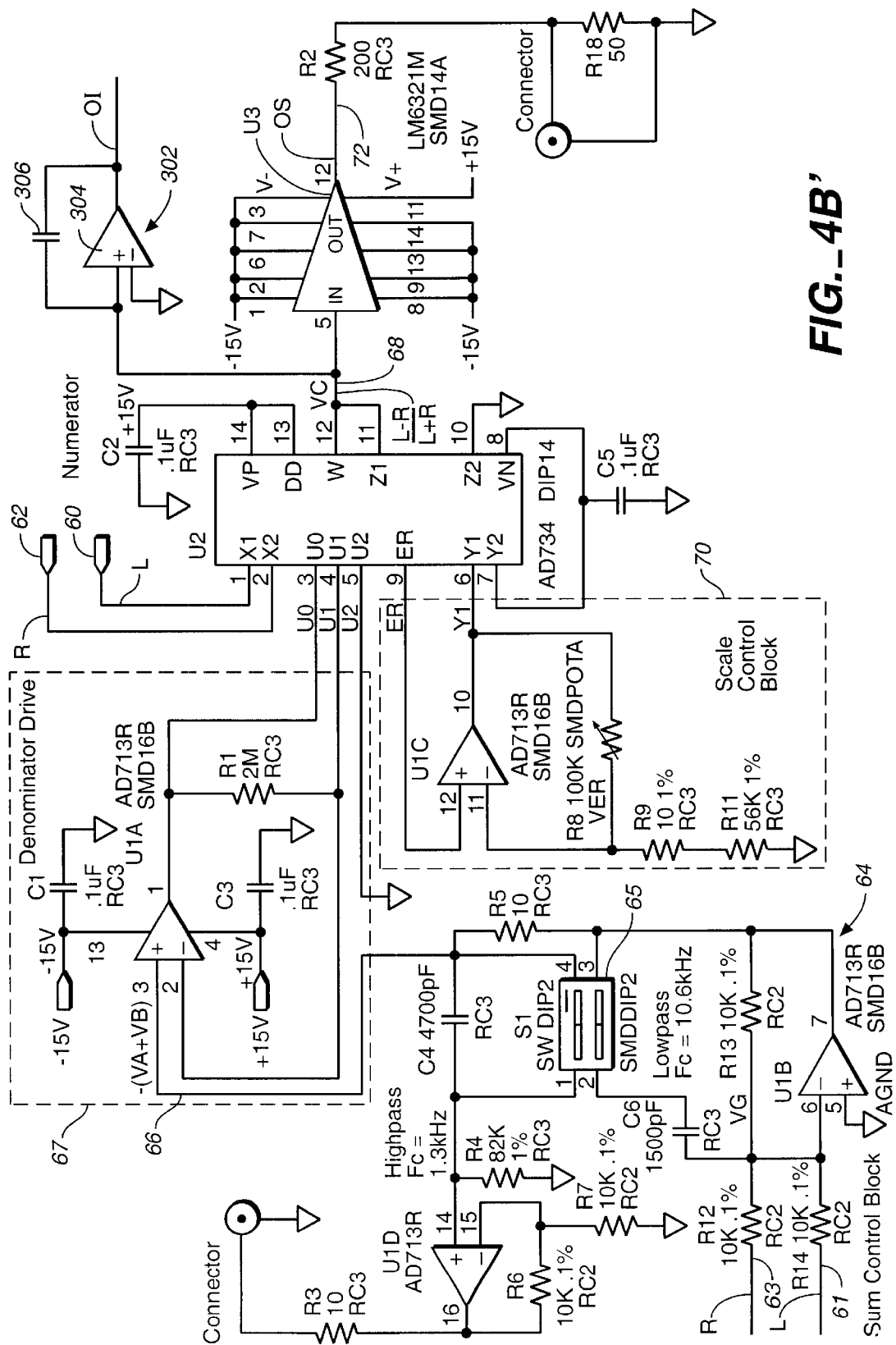
FIG._4B'

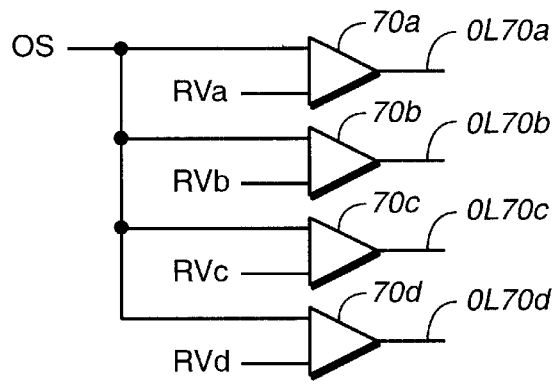
FIG._4C
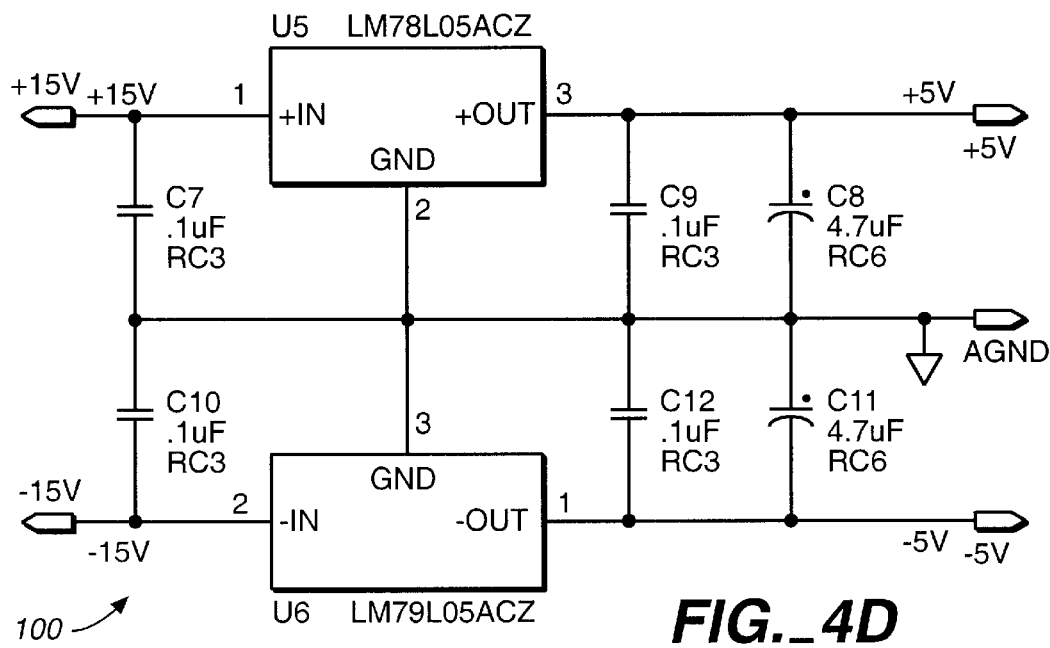
FIG._4D
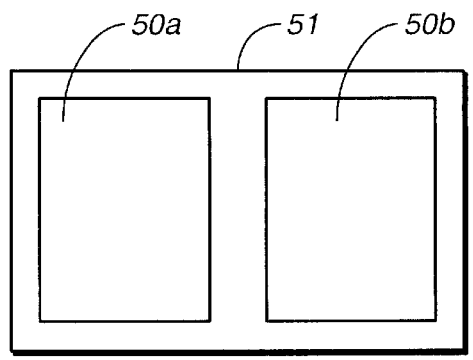
FIG._5

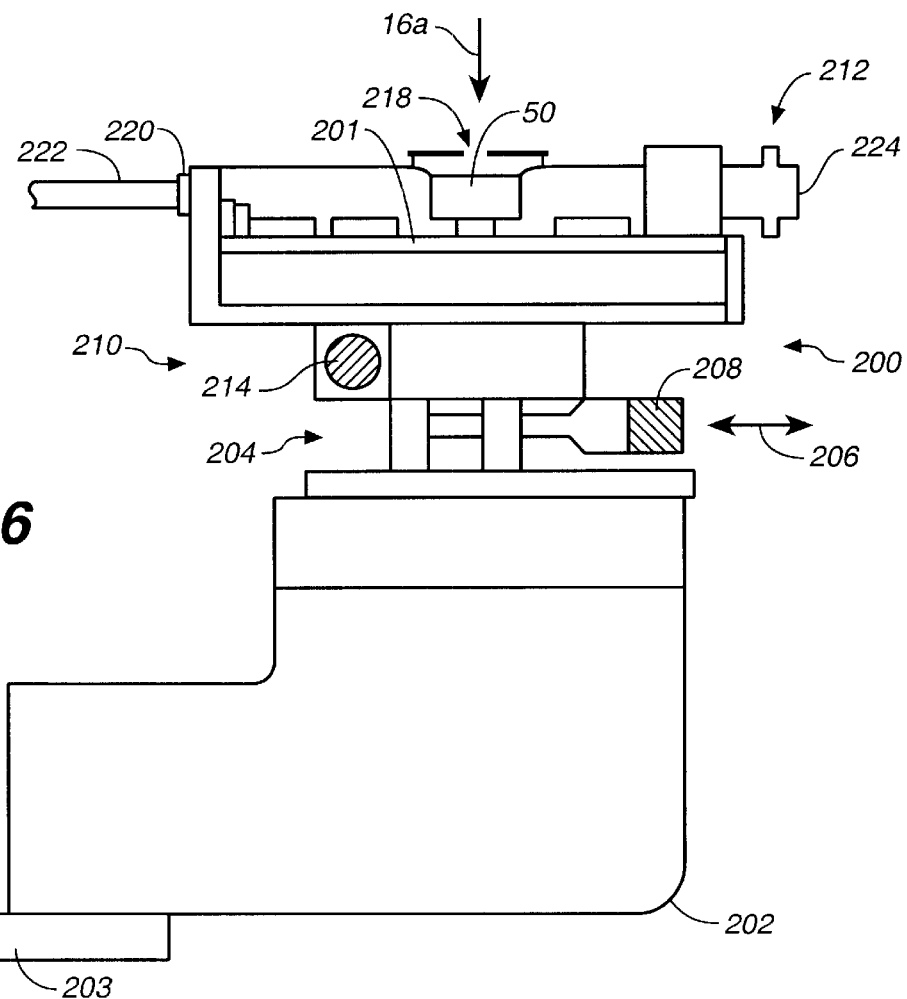
FIG._6
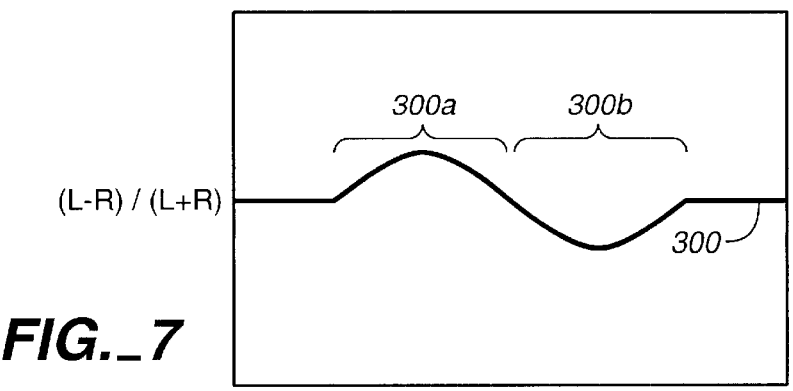
FIG._7

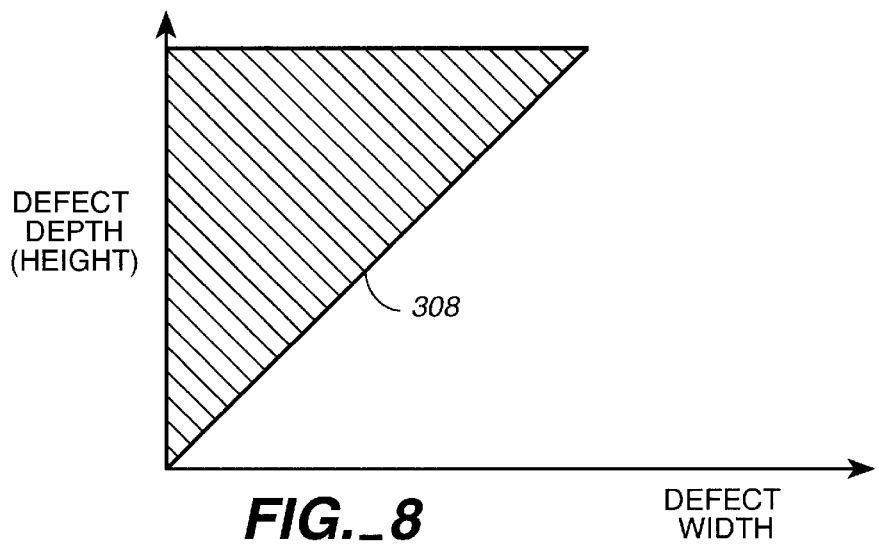
FIG._8
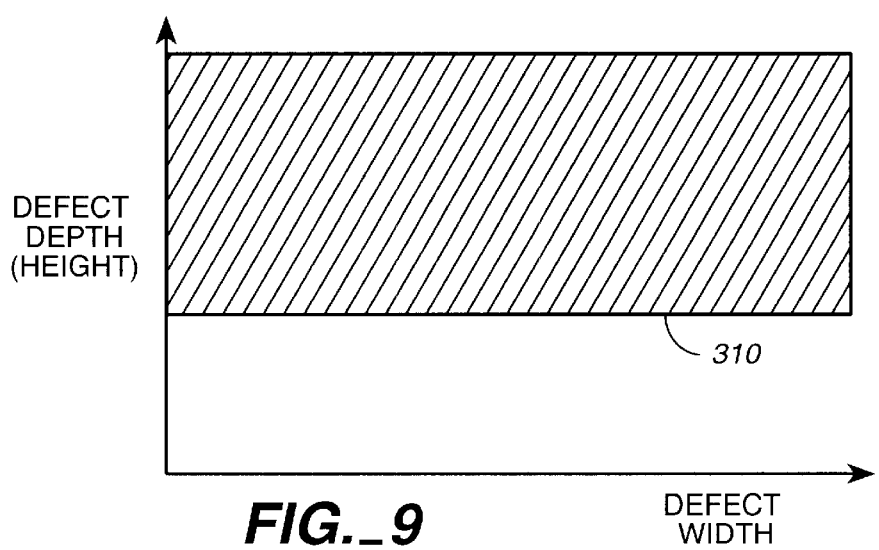
FIG._9
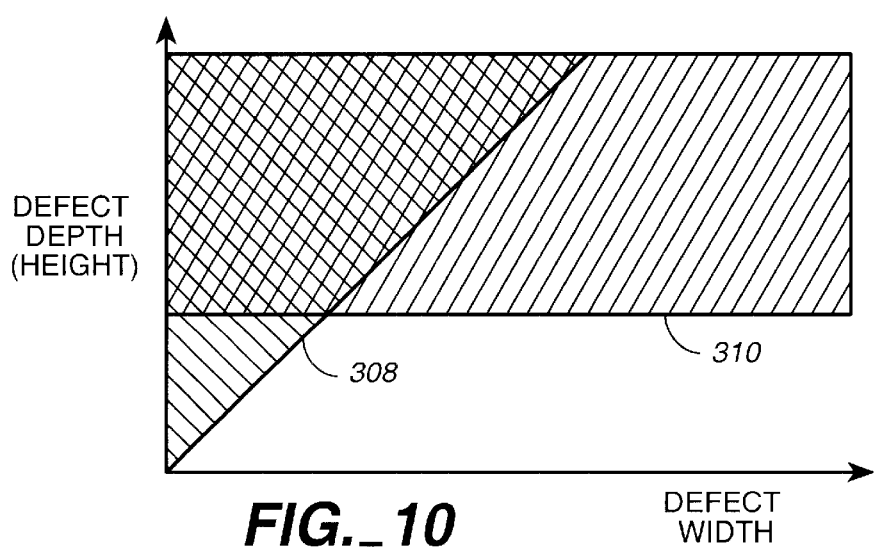
FIG._10

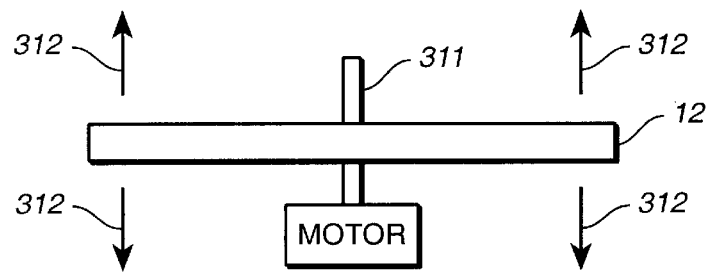
FIG._11
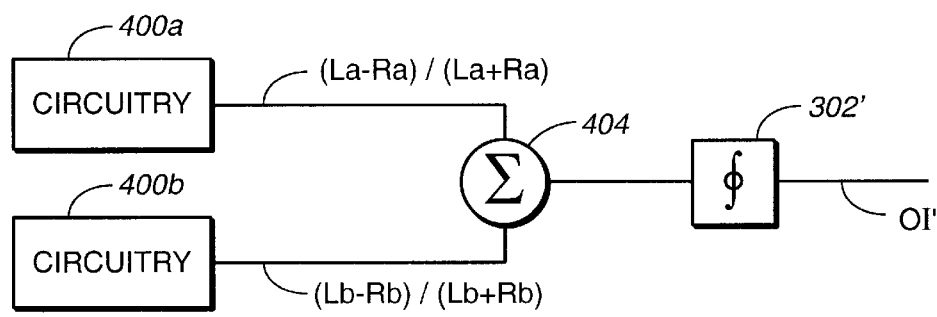
FIG._12A
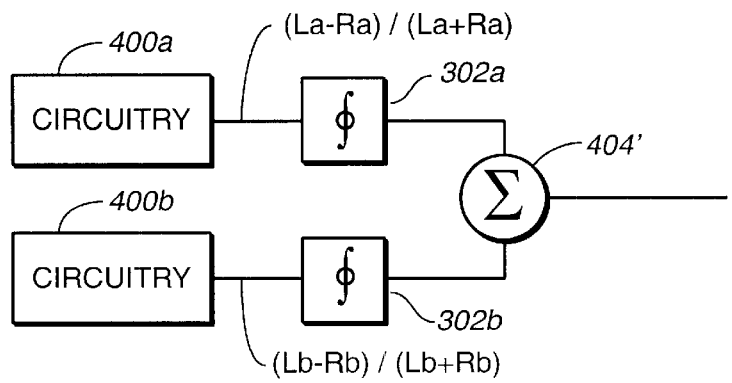
FIG._12B

METHOD AND APPARATUS FOR INSPECTING SUBSTRATES

This application is a continuation-in-part of U.S. patent application Ser. No. 09/337,709, filed Jun. 21, 1999 by Treves et al., incorporated herein by reference.

BACKGROUND OF THE INVENTION

This invention pertains to a method and apparatus for inspecting substrates used during the manufacture of magnetic disks.

Magnetic disks are typically manufactured by the following process:

1. An aluminum alloy substrate is electroless plated with NiP.
2. The plated substrate is polished.
3. The polished substrate is then textured, either mechanically or using a laser.
4. An underlayer (e.g. Cr or NiP), a magnetic alloy (typically a Co alloy) and a protective overcoat (typically carbon, hydrogenated carbon, or zirconia) are then sputtered, in that order, onto the substrate.
5. A lubricant is then applied to the protective overcoat.

The layers formed on magnetic disks (e.g. the underlayer, magnetic layer and overcoat) are extremely thin, e.g. on the scale of several tens of nanometers. It is very important that there be no or few large defects in the substrate prior to sputtering.

It is known in the art to use laser scanning systems to inspect magnetic disk substrates prior to sputtering. In these systems, a laser beam is reflected off of a substrate, and sensors such as photomultiplier tubes detect the reflected laser beam to determine whether defects are present on the substrate. Other systems use sensors other than photomultipliers to detect the reflected laser beam.

Examples of laser scanning systems include the PMT Pit Detector, the Diskan 6000, Diskan 9000 and Diskan 9001 systems manufactured by QC Optics of Burlington, Mass. Other prior art systems are discussed in U.S. Pat. Nos. 4,794,264; 4,794,265; and 5,389,794, each assigned to QC Optics.

FIG. 1 schematically illustrates a QC Optics Diskan 9001 apparatus 10 for detecting defects in a substrate, such as a substrate 12. Referring to FIG. 1, apparatus 10 comprises HeNe lasers 14a, 14b for generating laser beams 16a, 16b respectively. Laser beam 16a is used to scan across and inspect a top side 12a of substrate 12, while laser beam 16b is used to scan across and inspect a bottom side 12b of substrate 12. (Substrate 12 is typically rotated by a motor during this inspection, and laser beams 16a, 16b typically scan in the radial direction of the substrate.)

Laser beam 16a passes through a polarizer 18a, ¼ waveplate 20a, and a shutter 22a, reflects off a mirror 23a, passes through a lens 24a, a beam splitter 25a, and a lens 26a and reflects off of mirror 28a. Mirror 28a deflects laser beam 16a downward to substrate 12. Substrate 12 reflects laser beam 16a upwardly and back to mirror 28a, through lens 26a and back to beam splitter 25a. Beam splitter 25a deflects laser beam 16b to a photomultiplier tube 30a. Of importance, if laser beam 16a strikes a defect in substrate 12 (either a pit or a bump), that defect will reflect laser beam 16a at an angle. The fact that laser beam 16a is reflected at an angle is detected by photomultiplier tube 30a. In this way, apparatus 10 can use laser beam 16a to determine whether there are pits or bumps in substrate 12.

The manner in which a defect deflects a laser beam can best be understood by comparing FIGS. 2A and 2B. In FIG. 2A, laser beam 16a strikes a portion of substrate 12 where defect 32 deflects laser beam 16a at an angle θ. In contrast, in FIG. 2B, laser beam 16b strikes a portion of substrate 12 where there are no defects. Thus, in FIG. 2B, laser beam 16a reflects straight back, and not at an angle. As mentioned above, photomultiplier tube 30a detects whether or not laser beam 16a is reflected at an angle by a defect on substrate 12.

Referring back to FIG. 1, portions of laser beam 16a are also reflected past mirror 28a, pass through spacial filter 34a and lens 36a, and strike photomultiplier tube 38a. (Spacial filter 34a filters out light scattering caused by the texture pattern that is formed on substrate 12.) Of importance, photomultiplier tube 38a determines whether light is scattered by defects or contamination on substrate 12 at a wide angle.

The optical path for laser beam 16b is similar to the optical path of laser beam 16a, and will not be described in detail, except to note that it includes two mirrors 28b' and 28b'' instead of single mirror 28a.

FIG. 3 is a block diagram of the circuitry coupled to photomultiplier tubes 30a, 30b, 38a and 38b. As can be seen, each of photomultiplier tubes 30a, 30b, 38a and 38b is coupled to four comparators 42a–42d, 44a–44d, 46a–46d and 48a–48d, respectively. Each of comparators 42a–42d compares the output signal OS30a of photomultiplier tube 30a with an associated reference voltage RV42a–RV42d, and provides a binary output signal BOS42a–BOS42d in response thereto. Binary output signals BOS42a–BOS42d are stored in associated latches 52a–52d, the contents of which are loaded into a memory which can then be accessed by a central processing unit CPU (not shown). Comparators 44–48 similarly compare the output signals from photomultiplier tubes 30b, 38a and 38b to reference voltage signals RV, and generate binary output signals BOS in response thereto. These binary output signals are stored in latches 54–58, the contents of which can be accessed by central processing unit CPU to determine the size and character of a defect detected by the apparatus.

While apparatus 10 can detect some defects, it would be desirable to provide improved means for detecting such defects with greater sensitivity and accuracy. Co-pending patent application Ser. No. 09/337,709 discloses an improved circuit using a bi-cell photodetector for receiving a reflected laser beam and generating an output signal indicative of the presence of defects on a substrate in response thereto. In particular, the circuitry described in the '709 application generates an output signal indicative of the slope of the side of a defect wall. The '709 is more sensitive to the presence of defects than the FIG. 3 circuitry. However, it would be desirable to further improve the ability to detect defects.

SUMMARY

A method for detecting defects in a substrate comprises:
a) reflecting radiant energy off of a substrate (e.g. in the form of a laser beam);
b) generating a first signal indicative of the slope of the portion of the substrate surface reflecting said radiant energy; and
c) generating a second signal indicative of the height of the portion of the substrate surface in response to the first signal. In one embodiment, the second signal is the integral of the first signal.

If there is a defect at the portion of the substrate surface, the first signal indicates the slope of the defect, and the second signal indicates the height of the defect. Defective substrates are typically thrown out or reworked.

In accordance with another aspect of the invention, apparatus comprises means for detecting a laser beam reflected off the surface of a substrate. A first circuit within the apparatus generates a first signal indicative of the slope of the portion of the substrate where the laser strikes the substrate. A second circuit within the apparatus generates a signal indicative of the height of the portion of the substrate. In one embodiment, the second circuit functions as an integrator for integrating the first signal.

The first circuit is capable of detecting a first set of defects (i.e. defects having walls having a steepness exceeding a certain value), whereas the second circuit is capable of detecting a second set of defects (i.e. defects exceeding a certain height). By providing apparatus comprising both the above-mentioned first and second circuits, different types of defects can be detected, thereby enhancing the ability to screen out defective substrates early in the manufacturing process.

In one embodiment of the invention, the substrate is rotated during testing. During rotation, the substrate can vibrate. In accordance with one novel feature of the invention, the second circuit integrates a value corresponding to the slope a first surface of the substrate plus a value corresponding to the slope of a second surface of the substrate. The result of this integration is a value indicating the size of a defect on the substrate surface but canceling out anomalies in the value caused by substrate vibration.

These and other advantages of the invention will be better understood in light of the description below.

BRIEF DESCRIPTION OF THE DRAWINGS

FIG. 1 schematically illustrates an optical system using a laser beam to inspect a substrate for defects constructed in accordance with the prior art.

FIG. 2A illustrates a laser beam striking a defect on a substrate.

FIG. 2B illustrates a laser beam striking a portion of a substrate that does not contain a defect.

FIG. 3 is a block diagram of a prior art circuit for processing a signal from a set of photomultiplier tubes within apparatus 10 of FIG. 1.

FIGS. 4A to 4D are a schematic diagram of a circuit for processing a signal from a light sensing diode in accordance with the invention.

FIG. 4B' is a modified version of FIG. 4B including an integrator 302.

FIG. 5 illustrates in plan view a bi-cell photodiode used in the circuit of FIGS. 4A to 4D.

FIG. 6 illustrates a module containing some of the circuitry of FIGS. 4A to 4D.

FIG. 7 illustrates an output signal (L−R)/(L+R) generated by the circuitry of FIGS. 4A to 4D.

FIG. 8 schematically illustrates the set of defects that can be detected by the circuitry of FIGS. 4A to 4D without integrator 302 present.

FIG. 9 schematically illustrates the set of defects that can be detected by integrator 302.

FIG. 10 schematically illustrates the set of defects that can be detected with the combination of the circuitry of FIGS. 4A to 4D along with integrator 302.

FIG. 11 schematically illustrates a substrate vibrating during high speed rotation during inspection in accordance with one embodiment of the invention.

FIG. 12A is a block diagram of an embodiment of the invention in which an integrator and summing circuit are used to eliminate noise caused by substrate vibration.

FIG. 12B is a block diagram of another embodiment of the invention in which a pair of integrators and summing circuit are used to eliminate noise caused by substrate vibration.

DETAILED DESCRIPTION

Circuitry for Generating First Defect Detection Signal (L−R)/(L+R)

One embodiment of the invention uses most of the optical elements shown in FIG. 1. However, instead of using photomultiplier tubes 30 and the circuitry of FIG. 3, a new structure has been developed for detecting reflected laser beams 16 and generating an output signal to determine whether a defect is present on substrate 12. Specifically, instead of using photomultiplier 30a, a bi-cell photosensitive diode 50 is used (FIGS. 4A and 5). Bi-cell photosensitive diode 50 comprises a diode 50a and a diode 50b. Diodes 50a and 50b are roughly rectangular, and are formed on a common substrate 51 adjacent to one another, as shown in FIG. 5. In one embodiment, bi-cell photosensitive diode 50 is device model number SPOT-2D, manufactured by UDT of Hawthorne, Calif. In another embodiment, bi-cell photosensitive diode 50 is device number SD 113-24-21-021, manufactured by Advanced Photonics of Camarillo, Calif. However, other types of photosensitive diodes, photosensitive transistors, or other devices may also be used.

FIGS. 4A to 4C schematically illustrate circuitry for processing the output signal of diodes 50a, 50b. This circuitry comprises numerous components, e.g. resistors, capacitors, and various integrated circuits. The value of these components, and the part number of these integrated circuits are set forth in Table I below.

Referring to FIG. 4A, the cathode of diodes 50a, 50b are connected to a bias circuit 52 comprising a resistor R16 connected to a 15 volt source, and a capacitor C16 connected to ground. The anode of diode 52a is coupled to a preamplifier 58a for generating signal R. Similarly, the anode of diode 52b is coupled to a preamplifier 58b for generating signal L. Signals L and R are voltages representing the amount of light striking diodes 50a and 50b, respectively.

Preamplifier 58a comprises an operational amplifier U7 having an inverting input lead $U7_2$ coupled to diode 50a and a non-inverting input lead $U7_3$ connected to ground. Output lead $U7_6$ is coupled to input lead $U7_2$ via resistor R15 (typically 15 kΩ). Of importance, because of the manner in which diode 50a is biased, it exhibits a low capacitance. (All diodes exhibit a certain amount of capacitance due to their pn junctions.) The capacitance exhibited by diode 50a depends upon the bias voltage applied across it. By applying a relatively large voltage across photodiode 50a, one can ensure that the capacitance of diode 50a is relatively low, e.g. below 13 pF. (For example, in one embodiment, the capacitance of diode 50a is between 0.1 and 13 pF. In another embodiment, the capacitance can be between 3 and 13 pF.) The capacitance of diode 50a and resistor R15 form an RC filter. By ensuring that the capacitance of diode 50a is low, the time constant of this RC filter will be low, enabling preamplifier 58 to provide a signal having a bandwidth of at least 100 kHz. (The bandwidth typically exceeds 200 kHz, and can be between 500 kHz and 100 MHz. For example, in one embodiment, the bandwidth is about 10 MHz.) This bandwidth increases the speed at which the apparatus can inspect a substrate for defects.

Signal L is provided at input leads 60 and 61, and signal R is provided at input leads 62 and 63 of the circuitry of FIG.

4B. As explained below, this circuitry provides an output signal OS, indicative of defects on substrate 12.

Of importance, if there is no defect present on substrate 12, the same amount of light should strike diodes 52a and 52b, and signals L and R should be equal. If there is a defect present on substrate 12, laser beam 16a will be deflected in one direction or another (left or right), and one of signals L, R will be greater than the other signal R, L. As explained below, the circuitry of FIG. 4B provides a signal that is a measure of the difference between signals L and R. This signal is related to the extent to which a defect in substrate 12 deflects light to the left or right when it bounces off the defect.

Of importance, the amount of light provided by laser 14 (FIG. 1) can vary, thereby injecting noise into signals L and R. Such noise tends to obscure the ability to detect and measure defects in substrate 12. Also, different substrates can exhibit different amounts of reflectivity. This reflectivity variation can also obscure the ability to detect and measure defects in substrate 12. Accordingly, the circuit of FIG. 4B includes a sum amplifier 64 that generates a normalizing signal L+R at a lead 66 of a drive circuit 67. Drive circuit 67 amplifies signal L+R and provides the amplified normalizing L+R signal to an integrated circuit U2. (Drive circuit 66 has drive characteristics that match the requirements of integrated circuit U2.)

Sum circuit 64 includes a set of switches 65. Switches 65 permit one to adjust a filter time constant exhibit by sum circuit 64. This permits one to either detect or ignore stain regions of varying reflectivity on substrate 12, depending upon the setting of switches 65.

Sum circuit 64 also includes an amplifier U1D for providing an output signal on a lead 69. Buffer U1D provides another signal indicative of the magnitude of L+R. This signal can be used to determine when the laser beam strikes the end of substrate 12 as the laser scans across the substrate.

Circuit U2 receives the amplified normalizing signal L+R and signals L and R. Circuit U2 provides a signal equal to (L−R)/(L+R) on a lead 68. Signal (L−R)/(L+R) is a measure of the extent to which a defect deflects light to the left or to the right, corrected for any change in the total strength of signals L and R caused by laser power fluctuation or changes in disk surface reflectivity.

Integrated circuit U2 also receives voltage signals ER, Y1 and Y2 from an amplifier circuit 70. Signals Y1 and Y2 permit adjustment of an amplification constant used by integrated circuit U2. (This amplification is proportional to signals Y1−Y2.) Of importance, if the gain is too high, it can cause instability in circuit U2.

Signal (L−R)/(L+R) is provided to an amplifier U3, which provides an output signal OS at an output lead 72. Output signal OS is coupled to a set of comparators 70a, 70b, 70c and 70d, which compare signal OS to reference voltages RVa, RVb, RVc and RVd, respectively (FIG. 4C). If laser beam 16 is not deflected by a defect on substrate 12, signal OS will be less than any of voltages RVa to RVd. If laser beam 16 is slightly deflected by a defect, signal OS will exceed reference voltage Rva, and comparator 70a will provide an active binary output signal at an output lead OL70a, while concurrently, the output of comparators 70b'70d will be inactive. If laser beam 16 is deflected to a greater extent, signal OS will exceed reference voltage RVb, causing the binary output signal of comparator 70b to go active. Comparators 70c and 70d function in a similar manner. Thus, comparators 70a to 70d provide a measure of the extent to which laser beam 16 is deflected by defects on substrate 12. (This, in turn, is a measure of the steepness of the defect walls, which is important because the steepness of the walls is a measure of the size of the defect.) The binary output signals on leads OL70a to OL70d are coupled to latches which can be processed by circuitry similar to that used to process signals BOS421−BOS48d, described above.

FIG. 4D illustrates power supply circuitry 100 used by the circuitry of FIGS. 4A and 4B. Circuitry 100 receives input voltages of 15V and −15V, and generates therefrom output voltages of 5 volts, ground and −5 volts. Circuitry for providing such output voltages are known to those skilled in the art, and thus this circuitry will not be described in further detail.

The bi-cell photodiode 50 and associated circuitry of FIGS. 4A to 4D can be used to replace photomultiplier tubes 14a, 14b. However, in one embodiment, photomultiplier tubes 38a, 38b are used to detect wide angle scattering of light as discussed above.

FIG. 6 is a cross section view of a module 200 containing a printed circuit board 201 that carries bi-cell photodiode 50 and a portion of the circuitry of FIGS. 4A to 4D. Module 200 is mounted on a block 202 coupled to a holder 203. Module 200 includes a first mechanism 204 for making fine position adjustments of bi-cell photodiode 50 in the direction of arrow 206. Such adjustments are controlled by turning a first control screw 208. Mounted on first mechanism 204 is a second mechanism 210 for making fine position adjustments of bi-cell photodiode 50 in a direction perpendicular to arrow 206. These adjustments are controlled by turning a second control screw 214. (Control screw 214 is perpendicular to control screw 208.) A bock 212 is affixed to second mechanism 210. PC board 201 is mounted within block 212.

Bi-cell photodiode 50 is located in a central portion of PC board 201. Block 212 contains a window 218 for permitting laser 16a to strike photodiode 50. (As mentioned above, laser 16a is reflected off of the substrate being tested for defects.) Block 212 includes a first connector 220 for receiving electrical power via a wire 222 and a second connector 224 for providing signal L+R. Another connector within block 212 (not shown) provides signal L−R/L+R. These signals are processed by circuitry outside of block 212 in the manner discussed above.

Embodiment Comprising an Integrator For Generating Signal $f(L-R)/(L+R)dt$

Signal (L−R)/(L+R), provided by the circuitry of FIGS. 4A to 4D, is a measure of the slope of the defects on substrate 12. Specifically, referring to FIG. 2A, if a laser beam 16a strikes defect 32, signal (L−R)/(L+R) produced by the circuitry of FIGS. 4A to 4D is a measure of the slope of defect 32 at the point where laser beam 16a strikes defect 32. For example, assume that defect 32 has a profile as shown in FIG. 2A. Therefore, as defect 32 moves in a direction D past laser beam 16a (i.e. because substrate 12 rotates during testing), output signal (L−R)/(L+R) will appear as shown in FIG. 7. This signal includes a first portion 300a generated when laser beam 16a strikes the leading side 32a of defect 32 and a second portion 300b generated when laser beam 16 strikes the trailing side 32b of defect 32. In other words, signal (L−R)/(L+R) is proportional to dy/dx, where y is the height of the defect surface as a function of the position of substrate 12 in the x direction.

In accordance with one embodiment of the invention, an integrator 302 is coupled to receive signal (L−R)/(L+R) (see FIG. 4B') to generate another output signal OI that is the integral of signal (L−R)/(L+R) with respect to time. FIG. 4B' illustrates integrator 302 as an operational amplifier 304 with capacitive feedback path 306. However, in one embodiment, integrator 302 can be a circuit such as board no. QCO 9002.2, manufactured by QC Optics. Of importance, integrator 302 dramatically increases the ability of the apparatus to detect defects. This can be seen by comparing FIG. 8 (showing the set of defects that can be detected by the apparatus of FIGS. 4A to 4D with integrator 302 absent) with FIG. 9 (showing the set of defects that can be detected by integrator 302). In FIG. 8, with integrator 302 absent, the apparatus can detect defects in which the defect wall exceeds a particular slope. Thus, the apparatus can detect defects in a region 308. However, if a defect has a very gradual slope, it cannot be detected by the apparatus.

Integrator 302 can detect those defects having a height greater than a threshold, e.g. those defects in a region 310 shown in FIG. 9. Thus, by providing apparatus comprising both the circuitry of FIGS. 4A to 4D and integrator 302, a greater range of defects can be detected than apparatus lacking integrator 302. (See FIG. 10, which shows the range of defects that can be detected by circuitry in accordance with the invention, comprising both integrator 302 and the circuitry of FIGS. 4A to 4D.)

Embodiment for Canceling Anomalies Caused by Disk Vibration

During testing for defects in accordance with the invention, substrate 12 is typically rotated very rapidly by a motor, e.g. at about 12,000 rpm. This is considerably greater than the rotational velocity of a magnetic disk in a disk drive. (Disks in disk drives presently rotate at velocities on the order of about 7000 rpm.) At this high rotational velocity (12000 rpm), substrate 12 typically vibrates as it rotates about a spindle 311, e.g. as schematically shown by arrows 312 in FIG. 12A. It would be highly desirable for the circuitry of FIGS. 4A to 4D to be able to distinguish between changes in the y position of the substrate surface caused by vibration and changes in the y position of the substrate surface caused by defects. In accordance with one aspect of the invention, integrator 302' is connected in a novel manner for generating a signal indicative of the presence of defects on substrate 12 without having substrate vibration degrade the accuracy of defect detection.

Referring to FIG. 12A, apparatus in accordance with the invention comprises first circuitry 400a for detecting defects on top side 12a of substrate 12 and second circuitry 400b for detecting defects on bottom side 12b of substrate 12. First and second circuitry 400a, 400b are identical to what is shown in FIGS. 4A to 4D. In this embodiment, signal (La−Ra)/(La+Ra) is generated by circuitry 400a and signal (Lb−Rb)/(Lb+Rb) is generated by circuit 400b. Signal (Lb−Rb)/(Lb+Rb) is summed with signal (La−Ra)/(La+Ra) by a summing circuit 404, and this sum is integrated by an integrator 302'. (Integrator 302' can be device QCO 9002.2, manufactured by QC Optics.) Integrator 302' provides an output signal OI' as follows:

$$OI' = \int [((La-Ra)/(La+Ra)) + ((Lb-Rb)/(Lb+Rb))] dt$$

Signal OI' is a measure of the height of defects on both surfaces of substrate 12. Of importance, if substrate 12 is displaced because of vibration in the direction of arrow 402, that would distort the first term in the above intergral (i.e. it would distort ((La−Ra)/(La+Ra)). However, such vibration will not distort $\int[((La-Ra)/(La+Ra))+((Lb-Rb)/(Lb+Rb))]$ dt. This is because any distortion in the first term of the integral will be counterbalanced by an equal and opposite distortion in the second term of the integral. Accordingly, the circuit of FIG. 12A can detect the presence of defects in the surfaces of substrate 12 despite vibration of substrate 12 during rotation.

In another embodiment, instead of integrating the sum of signal [(La−Ra)/(La+Ra)]+[(Lb−Rb)/(Lb+Rb)], two separate integrators 302a, 302b are provided (FIG. 12B). The first integrator generates a signal corresponding to the integral of signal (La−Ra)/(La+Ra) and a second integrator generates a signal corresponding to the integral of signal (Lb−Rb)/(Lb+Rb). The first and second integrals are summed by a summing circuit 404'. In other words, the summing circuit generates a signal equal to:

$$OI'' = \int [(La-Ra)/(La+Ra)] dt + \int [(Lb-Rb)/(Lb+Rb)] dt.$$

(Of course, signal OI' and OI'' are equivalent.) Signal OI' (or signal OI'') is used to evaluate the acceptability of the substrate being tested in the same manner as signal OI discussed above. However, signals OI' and OI'' are substantially unaffected by substrate vibration.

It should be noted that if the position of diodes 50a and 50b are reversed for the sensor on side 12a of substrate 12, the polarity of signal (La−Ra)/(La+Ra) will be reversed. Thus, instead of adding signal (La−Ra)/(La+Ra) to signal (Lb−Rb)/(Lb+Rb), one would either a) subtract one signal from the other; or b) invert one signal prior to adding it to the other. (One could perform integration either before or after such subtraction or inversion.) However, all of these operations are essentially equivalent. In particular, these operations all amount to combining the signals from the sensors on each side of the substrate in a manner that permits detection of defects in the substrate surface but cancels out distortion that would otherwise be caused by vibration or flutter.

Processing of Substrate 12 After Testing for Defects

After a substrate is inspected with the apparatus and method of the present invention, the substrate is typically used to manufacture a magnetic disk. During this process, an underlayer, a magnetic layer, and a protective overcoat are deposited, e.g. by sputtering or evaporation, onto the substrate. A lubricant layer is then applied to the overcoat. An example of a process for completing the manufacture of a magnetic disk after substrate inspection is set forth in U.S. patent application Ser. No. 08/984,753, filed by Bertero, et al., assigned to the assignee of the present invention and incorporated herein by reference.

While the invention has been described with respect to a specific embodiment, those skilled in the art will appreciate that changes can be made in form and detail without departing from the spirit and scope of the invention. For example, different types of lasers (e.g. diode lasers or gas lasers) can be used to inspect a substrate in accordance with the invention. Further, this structure can be used to test different kinds of substrates, e.g. glass or glass ceramic substrates. Such substrates can be used to manufacture magnetic disks or other devices. Accordingly, all such changes come within the present invention.

TABLE I

| Component | Value | Component | Value |
| --- | --- | --- | --- |
| R1 | 3 MΩ | C1 | 0.1 μF |
| R2 | 200Ω | C2 | 0.1 μF |
| R3 | 10Ω | C3 | 0.1 μF |
| R4 | 82KΩ | C4 | 4700 pF |
| R5 | 10Ω | C5 | 0.1 μF |
| R6 | 10KΩ | C6 | 1500 pF |
| R7 | 10KΩ | C7 | 0.1 μF |
| R8 | 100KΩ variable resistor | C8 | 4.7 μF |
| R9 | 10Ω | C9 | 0.1 μF |
| R11 | 56KΩ | C10 | 0.1 μF |
| R12 | 10KΩ | C11 | 4.7 μF |

TABLE I-continued

| Component | Value | Component | Value |
|---|---|---|---|
| R13 | 10KΩ | C12 | 0.1 μF |
| R14 | 10KΩ | C13 | 1 pF |
| R15 | 15KΩ | C14 | 0.1 μF |
| R16 | 10KΩ | C15 | 0.1 μF |
| R17 | 15KΩ | C16 | 0.1 μF |
| R18 | 50Ω | C17 | 1 pF |
| R16 | 10KΩ | C18 | 0.1 μF |
|  |  | C19 | 0.1 μF |

| Integrated Circuit | Model | Manufacturer |
|---|---|---|
| U1A, U1B, U1C | AD713R-16 | Analog Devices |
| U2 | AD734 | Analog Devices |
| U3 | LM6321M | National Semiconductor |
| U5 | LM78L05ACZ | National Semiconductor |
| U6 | LM79L05ACZ | National Semiconductor |
| U7 | OPA655 | Burr Brown |
| U9 | OPA655 | Burr Brown |

We claim:

1. A method for detecting defects on a workpiece, said method comprising:
   providing a first signal indicative of the slope of said workpiece;
   providing a second signal that is the integral of said first signal;
   providing a first determination of whether a defect exists in said workpiece in response to said second signal; and
   providing a second determination of whether a defect exists in said workpiece in response to said first signal without using said second signal.

2. Method of claim 1 further comprising directing radiant energy to said workpiece and detecting the reflection of said radiant energy from said workpiece, said act of providing a first signal being performed in response to the detection of the reflection of said radiant energy.

3. Method of claim 2 wherein said radiant energy is in the form of a laser beam.

4. A method for detecting defects on a workpiece, said method comprising:
   providing a first signal indicative of the slope of said workpiece;
   providing a second signal that is the integral of said first signal;
   comparing said first signal against at least a first threshold value; and
   comparing said second signal against at least a second threshold value, wherein if said first signal exceeds said first threshold value or said second signal exceeds said second threshold value a defect is considered to be present in said workpiece.

5. Method of claim 4 wherein said first signal is generated in response to a bi-cell detector, said bi-cell detector comprising first and second cells formed on a common substrate, said first signal being a measure of the amount of reflected radiant energy striking said first cell minus the amount of reflected radiant energy striking said second cell.

6. Method of claim 1 wherein said workpiece is a substrate used in the manufacture of a magnetic disk.

7. Method comprising:
   moving a workpiece;
   reflecting first radiant energy off a first side of said workpiece;
   reflecting second radiant energy off a second side of said workpiece;
   generating a first signal indicative of the slope of the surface of said first side in response to said reflected first radiant energy;
   generating a second signal indicative of the slope of the surface of said second side in response to said reflected second radiant energy; and
   generating a third signal indicative of the integral of a combination of said first and second signals, said third signal representing the presence of defects in said first and second sides of said workpiece.

8. Method of claim 7 wherein said generating of said third signal comprises summing said first and second signals to generate a sum signal, and integrating said sum signal.

9. Method of claim 7 wherein said generating of said third signal comprises generating the integral of the first signal, generating the integral of the second signal, and summing the integral of the first signal and the integral of the second signal.

10. Method of claim 7 wherein said third signal indicates the presence of defects on the first and second sides of said workpiece while reducing distortion caused by vibration of said workpiece.

11. Method of claim 7 wherein said workpiece is a substrate used for magnetic disk manufacturing and said first and second radiant energy comprise laser beams and said moving of said workpiece comprises rotating said substrate.

12. Apparatus comprising:
   a first circuit for generating a first signal indicative of the slope of the surface of a workpiece; and
   a second circuit for generating a second signal that is the integral of the first signal;
   a third circuit for sensing whether a defect is present on said surface in response to said second signal; and
   a fourth circuit for sensing whether a defect is present on said surface in response to said first signal independent of said second signal.

13. Apparatus of claim 12 wherein said workpiece is a substrate used in the manufacture of magnetic disks.

14. Apparatus of claim 12 further comprising:
   a source of radiant energy, said radiant energy being reflected off said workpiece; and
   a sensor for sensing said radiant energy reflected off said workpiece, said sensor providing an output signal to said first circuit, said first circuit generating said first signal in response to said output signal.

15. Apparatus comprising:
   a first circuit for generating a first signal indicative of the slope of the surface of a workpiece;
   a second circuit for generating a second signal that is the integral of the first signal; and
   a comparator comparing the first and second signals to one or more reference signals to detect whether there is a defect on the surface of the workpiece.

16. Apparatus comprising:
   a first circuit for generating a first signal indicative of the slope of the surface of a first side of a workpiece;
   a second circuit for generating a second signal indicative of the slope of the surface of a second side of the workpiece; and
   an integrator for generating a third signal corresponding to the integral of the first signal combined with the second signal.

17. Apparatus of claim 16 wherein the workpiece is a substrate used in the manufacture of magnetic disks.

18. Apparatus of claim 16 wherein said third signal provides a measure of defects in the surface of the workpiece that is substantially insensitive to vibration of said workpiece.

19. Apparatus comprising:

a first circuit for generating a first signal indicative of the slope of the surface of a first side of a workpiece;

a second circuit for providing a first integral signal that is the integral of the first signal;

a third circuit for generating a second signal indicative of the slope of the surface of a second side of the workpiece;

a fourth circuit for providing a second integral signal that is the integral of the second signal; and a circuit for combining the first and second integral signals.

20. Apparatus of claim 19 wherein the workpiece is a substrate used in the manufacture of magnetic disks.

21. Apparatus of claim 19 wherein the signal provided by said circuit for combining provides a measure of defects in the surface of the workpiece that is substantially insensitive to vibration of said workpiece.

* * * * *